United States Patent [19]
Liotta

[11] 3,932,220
[45] Jan. 13, 1976

[54] METHOD FOR ISOLATING BACTERIAL COLONIES

[76] Inventor: Lance A. Liotta, 14004 Mont Ave., East Cleveland, Ohio 44112

[22] Filed: Jan. 15, 1973

[21] Appl. No.: 323,584

Related U.S. Application Data

[62] Division of Ser. No. 62,810, Aug. 11, 1970, abandoned.

[52] U.S. Cl. ........................................ 195/103.5 R
[51] Int. Cl.² .......................................... C12K 1/04
[58] Field of Search ............. 195/103.5 R, 127, 139, 195/116

[56] References Cited
UNITED STATES PATENTS
2,771,398  11/1956  Snyder ........................ 195/103.5 R Primary Examiner—Lionel M. Shapiro
Assistant Examiner—Robert J. Warden
Attorney, Agent, or Firm—Fay & Sharpe

[57] ABSTRACT

The specification and drawings disclose methods and apparatus for separating and/or isolating bacteria and tissue cells for testing or rapid automatic scanning. The invention uses an expansible membrane on which the tissue cell or bacteria sample is placed and thereafter expanded to cause the sample to be separated. Apparatus is disclosed for facilitating stretching of the membrane and automatically scanning it.

6 Claims, 25 Drawing Figures

U.S. Patent   Jan. 13, 1976   Sheet 1 of 5   3,932,220
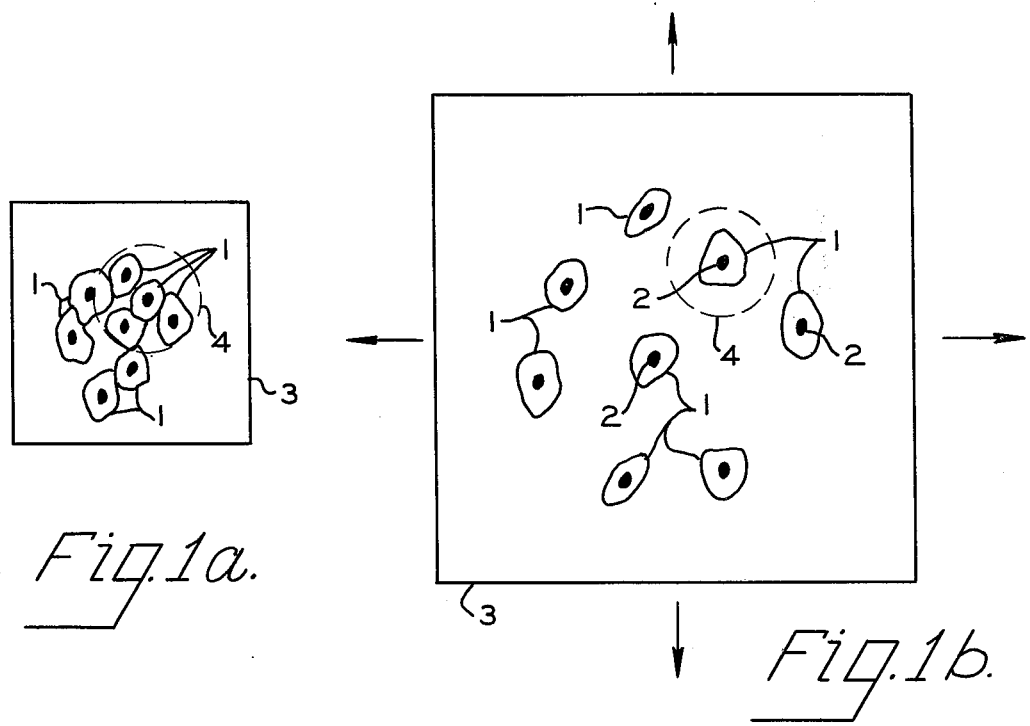
Fig.1a.
Fig.1b.
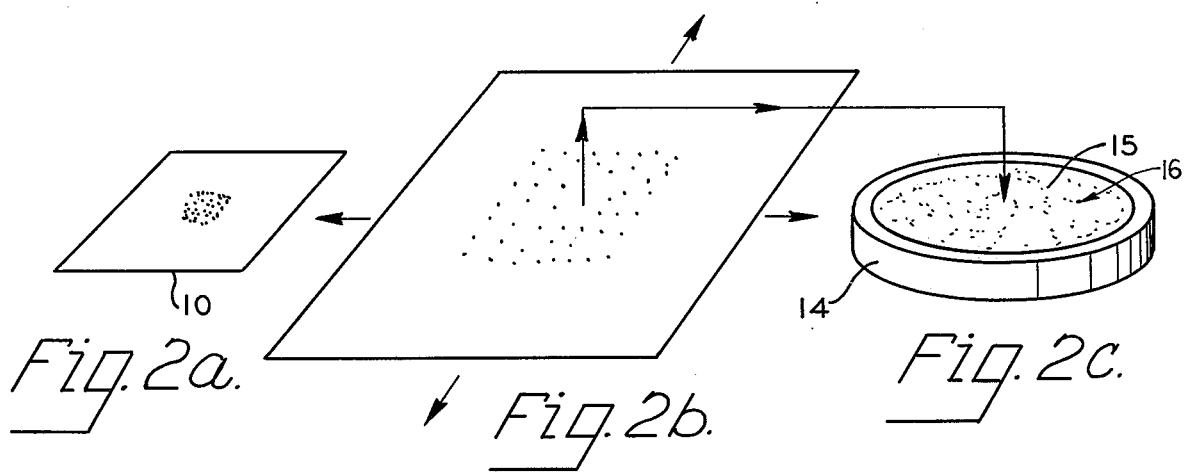
Fig.2a.
Fig.2b.
Fig.2c.
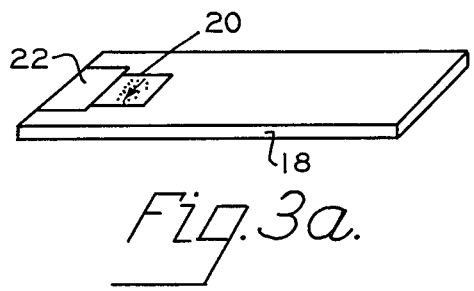
Fig.3a.
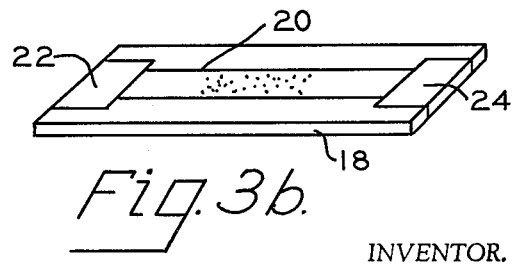
Fig.3b.
INVENTOR.
LANCE A. LIOTTA
BY
Fay, Sharpe & Mulholland
ATTORNEYS.

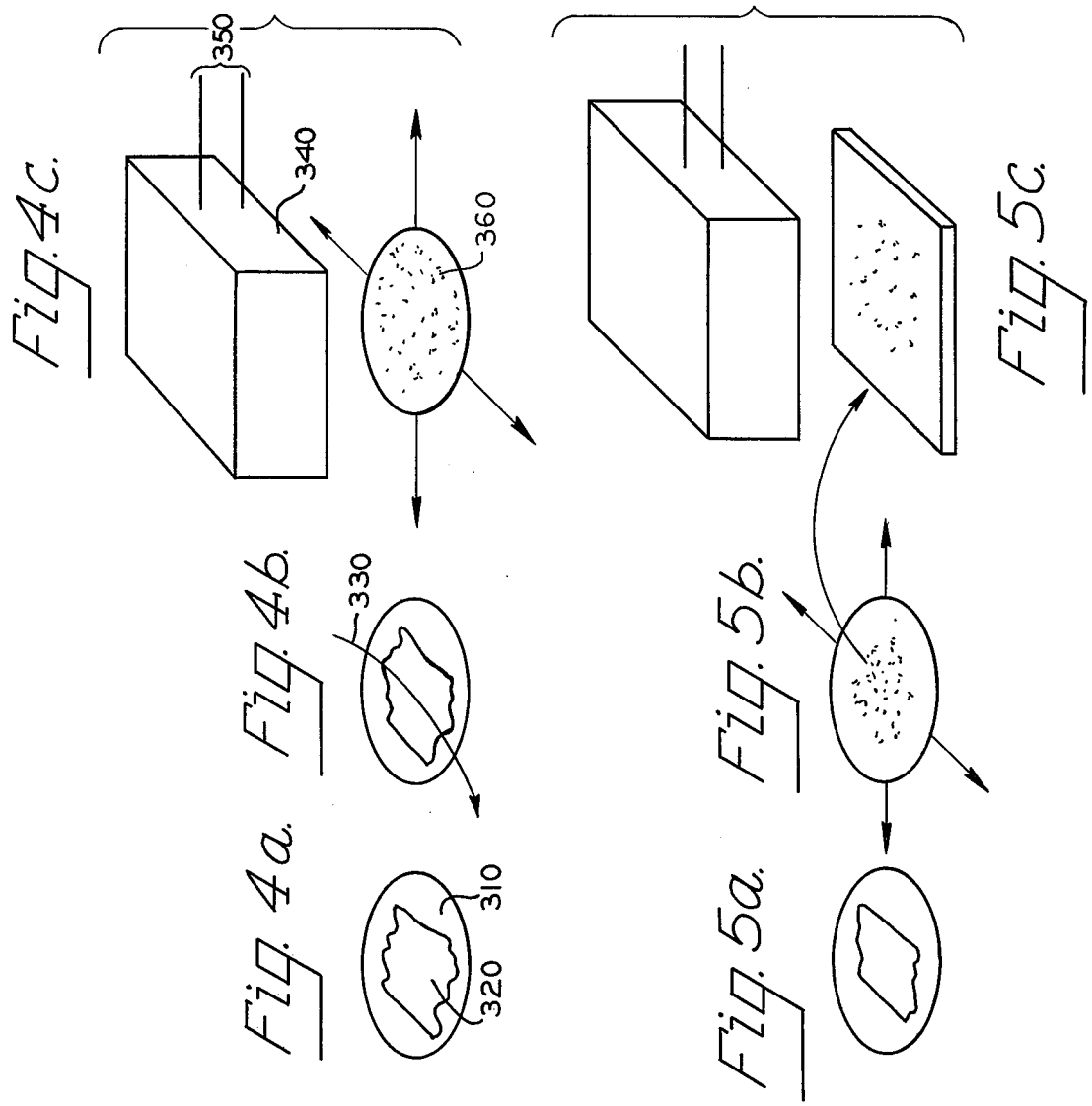

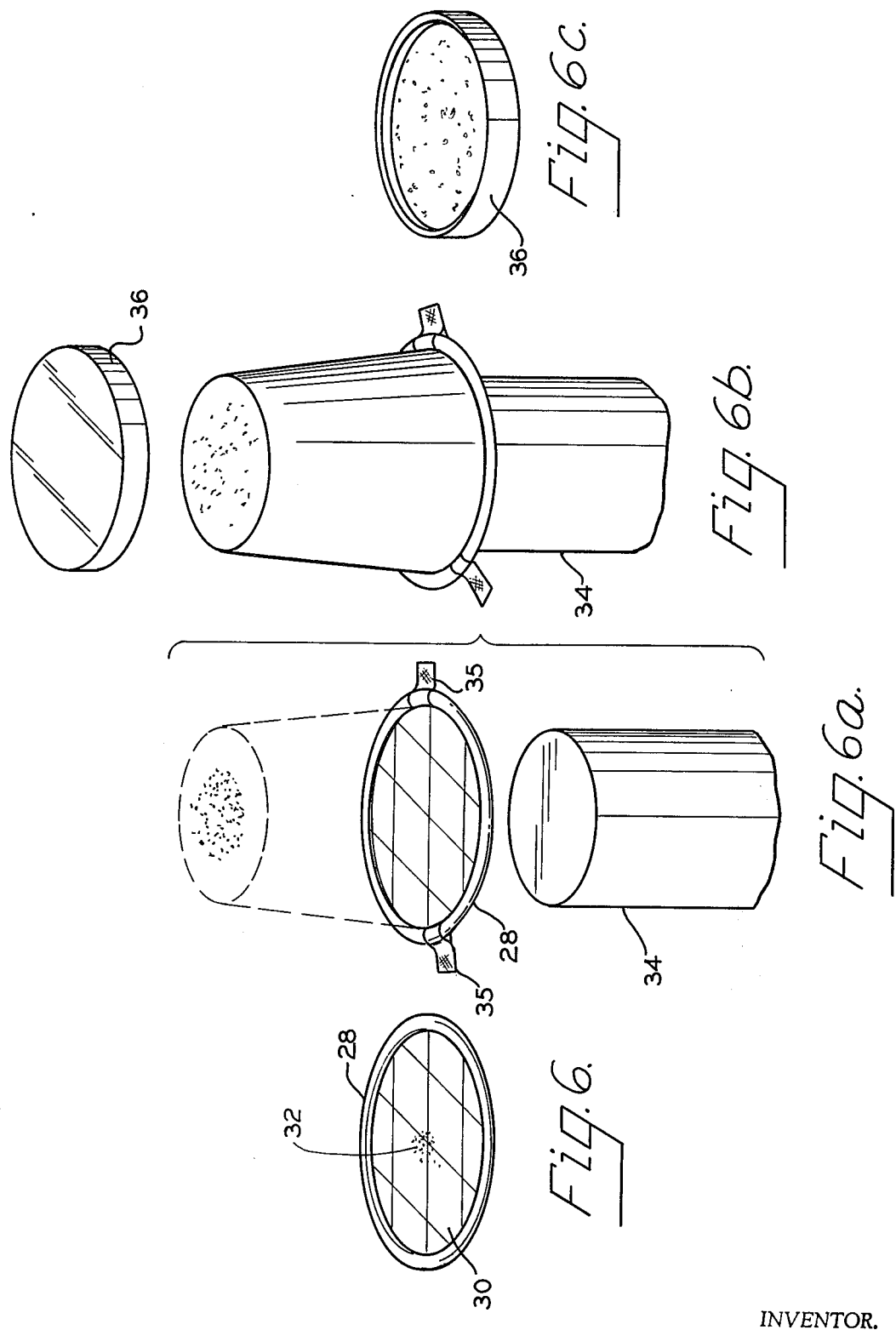

INVENTOR.
LANCE A. LIOTTA

BY
Fay, Sharpe & Mulholland
ATTORNEYS.

METHOD FOR ISOLATING BACTERIAL COLONIES

This is a division of application Ser. No. 62,810, filed Aug. 11, 1970, now abandoned.

The subject invention is directed toward the art of biological testing and, more particularly, to an improved method and apparatus for performing diagnostic cytology or microbiological tests.

The invention will be described with particular reference to its use in automatically isolating and characterizing cells for pathological evaluation, as well as isolating bacteria from a sample and transferring the isolated bacteria to test growth media; however, as will become apparent, the invention is capable of broader application and could be used for other types of tests and procedures.

One of the major obstacles to automation of cytology or microbiological diagnostic testing procedures has been the inherent difficulty of isolating individual bacteria and tissue cells so that they can be scanned by automatic scanning equipment. Normally, complicated and time consuming procedures including substantial manual intervention are required to obtain proper isolation.

In the case of bacteria, there are several isolating techniques which have been used with various degrees of success. One technique which is often used is streaking out a plate in a Petri dish. Generally, the culture medium in the Petri dish is streaked with a swab which has been dipped, for example, in a sample of a patient's body fluid or secretion. The streaking of the swab causes the amount of bacteria on the swab to be progressively diluted. If properly done, the bacteria colonies at the end of the streak are substantially isolated. It is somewhat difficult to assure good isolation by this technique, however, since only a small area at the end of the streak are properly isolated.

A second method sometimes used with bacteria, is to dilute the specimen in a sterile, inert liquid. The liquid is then poured or swabbed on the culture medium. Because of the dilution of the specimen, the individual bacteria colonies are relatively isolated. However, this procedure is messy and time consuming.

With tissue cells, the problem of isolating the cells for automatic scanning is substantially more difficult. This is, in part, because of the natural mutual adhesiveness of most normal cells. Generally, it can be accomplished only by manual intervention under microscopic examination, or by procuring the sample and disolving it in a liquid, then pumping the solution through a hole large enough for only one cell, and filtering or observing these cells one by one. The latter method though adapted to automation, requires a complicated sample procurement method, pumping (and backpumping because of clogging), and does not allow for chemical characterization of individual cells without elaborate filtering apparatus. Previous methods therefore are generally cumbersome and complicated.

It is known, however, that in neoplastic tissues, the cells have a greatly reduced mutual adhesiveness and that there are a great number of free cells. (For example, see the book "Diagnostic Cytology" by L. G. Koss and published by J. B. Lippincott Company, Philadelphia, 1968). This lack of mutual adhesiveness has been used as a test for cancerous tissue. The main technique has been to suspend a tissue sample in Hank's medium for a period of time, e.g. one-half hour, and observe the amount the tissue falls apart. As can be appreciated, this technique is time consuming and subject to substantial error.

The present invention provides methods and apparatus for rapidly isolating either bacteria or tissue cells and permitting automatic scanning. The method and apparatus, when used for bacteria isolation, allow uniform isolation of the sample over a substantial area rather than only at the end of a manual streak. The method is direct and requires no liquids, filtering, pumping, etc. Additionally, clinical non-aqueous and semi-solid samples such as mucous and lung sputum are easily isolated.

When the apparatus and method is used for isolating and characterizing biological cells for pathological evaluation, all chemical treatment, isolation and evaluation steps can be carried out without transferring the sample cells between different components, and without pumping, filtering, or manipulating any individual cells. Additionally, through the use of the inventive apparatus, it is possible to retain a hold on the cells for transportation, storage, and any number of future viewings or testing. Also, the apparatus allows all of the cells under consideration to be maintained in the same focal plane for easy scanning. Further, the apparatus permits any number of stain treatments and the like to be carried out.

In particular, and in accordance with one aspect of the invention, a method is contemplated for isolating biological cells, bacteria, and the like. The method includes the steps of:

a. providing a surface which can be expanded in at least one direction;
b. obtaining a sample of the material to be isolated;
c. placing at least a portion of the sample on the surface; and,
d. thereafter expanding the surface in at least one dimension by an amount sufficient to cause individual components in the sample to be moved finite distances apart.

As can be appreciated, the sample must normally be permitted to dry on the surface and to assure some adherence thereto. As the surface is expanded, the natural separation of the surface causes the material placed thereon to likewise be separated. Additionally, the stress applied to the surface is transmitted to the material causing internal stresses which tend to break the sample material apart. If the sample is bacteria, there is a low inherent adhesiveness between the individual bacteria which permits them to be easily pulled apart and isolated. Similarly, with certain types of abnormal cells, such as cancer cells, and cells included in human exfoliate samples, there is a low cell-to-cell adhesion and a large number of free cells which allows the cells to be pulled apart and/or isolated.

This method of isolation can be used to separate exfoliate cells for individual characterization, and in particular, for automatic optical measurements. In order to make any diagnostic detection of abnormal cells, sample cells must be isolated so that measurements can be made on one cell at a time. Any averaging of a measurement over more then one cell would be of insufficient accuracy to make any judgment of abnormality.

This method of isolation can also be used to assess the degree of mutual adhesion between cells from a biopsy tissue sample in order to determine whether or not the tissue is cancerous or benign.

When the sample is a bacteria sample, it is possible to easily transfer the isolated cells on the surface to a growth culture medium. Additionally, one aspect of the invention contemplates that the growth culture apparatus will comprise a plate having a multiplicity of small recesses, grooves, or the like, formed in its surface. Each groove is provided with a growth media. By proper selection of the growth media, it is possible to provide a rapid test for a multiplicity of different bacteria from a single sample. Additionally, the invention contemplates that the growth culture media device can be quickly scanned by automatic electronic scanning equipment to give a rapid printout of the presence or the absence of particular strains of bacteria.

The invention also contemplates that the expanding membrane concept can provide a rapid method for testing cell-to-cell adhesion characteristics of animal cell tissue. This method comprises the steps of providing a membrane surface which can be expanded in at least one direction and distributing a sample of the tissue over the surface. With the surface in the unexpanded condition, the cells thereon are optically viewed to determine the postion and character of cells in a predetermined area. Thereafter, the surface is expanded and the cells again viewed to determine position and character of the cells in the previously viewed area. If the cells have separated into individual isolated cells, it is highly probable that the cells are of an abnormal character. However, if the cells are grouped together in clumps, it is a good indication that the cell tissue is normal.

This invention can serve as a means to isolate individual cells from any sample such that each cell can be separately and automatically viewed in rapid sequence for diagnostic purposes. Additionally, the method contemplates that the cells can be stained while they are on the expanded surface and preferably, a stain is used which affects the nucleus of the cells causing them to become fluorescent. As is known, a high nucleonic acid content in a cell is an indication of a pathologic abnormality such as a cancer neoplasm. The size of the nucleus will thus be reflected in the amount of stain absorbed and the level of fluorescence present in each cell. By scanning the isolated cells with a photodetector arrangement, the relative brightness of the individual fluorescing nuclei can be utilized to give a rapid indication of the presence or absence of abnormal cells.

In addition, it can be appreciated that the isolated cells can be cultured on the expanded membrane by the addition of a nutrient solution through or from above the membrane to the cells. The use for such a method would be in testing of the contact inhibition.

Accordingly, a primary object of the invention is the provision of a method and apparatus whereby biological cells, bacteria and the like can be easily and rapidly isolated.

An additional object of the invention is the provision of a method and apparatus for permitting automation of bacteriological testing through the use of an expanded membrane bacteria isolating technique.

A still further object is the provision of apparatus for automatically determining the presence or absence of abnormal cells in a cell sample, and in particular, a simple automatic screening procedure for cancer.

A still further object of the invention is a method of isolating cells from an exfoliate cell sample so that diagnostic measurements can be automatically applied to individual cells in rapid succession.

A still further object is the provision of a method for testing cell-to-cell adhesion characteristics of tissue from biopsies and the like and providing information as to whether or not a neoplasm is benign or malignant.

A still further object of the invention is the provision of a system for automatically scanning a bacterial growth assembly and indicating the presencr or the absence of selected types of bacteria cultures.

Yet another object is a provision of method and apparatus of the general type described which is simple to use and can rapidly perform tests which were heretofore extremely complex and time consuming.

A still further object is the provision of apparatus for automatically performing the noted methods.

These and other objects and advantages will become apparent from the following description when read in conjunction with the accompanying drawings wherein;

FIGS. 1A and 1B show a magnified representation of the isolation of biological cells with this method;

FIGS. 2A through 2C show a series of steps utilized in carrying out one method aspect feature of the invention;

FIGS. 3A and 3B show apparatus which can be used to practice the inventive method;

FIGS. 4A–4C and 5A–5C are pictorial illustrations of automatic apparatus particularly suited for use in practicing certain features of the inventive methods;

FIGS. 6–6C are pictorial illustrations of a sequence of steps utilizing a modified apparatus for carrying out one of the methods of the invention;

Figure 8:
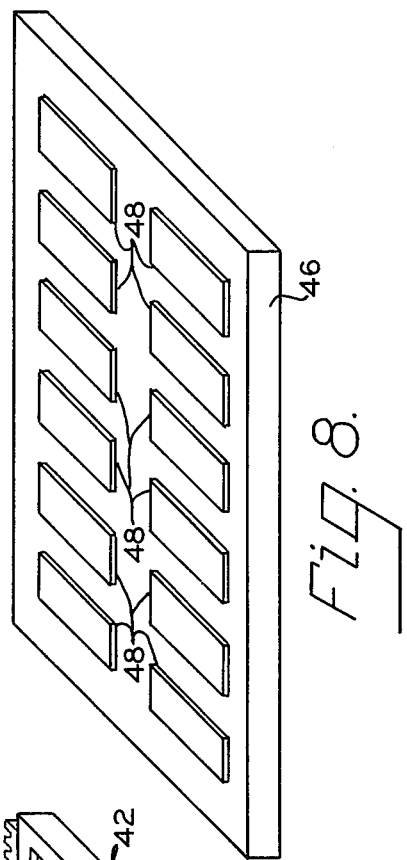
FIG. 8 is a modified form of bacterial growth culture apparatus which can be used in performing certain method aspects of the invention.

Referring more particularly to the drawings, the invention can best be understood by reference to FIGS. 1A and 1B which are basic cell isolation methods. As shown in FIG. 1A, biological cells 1 have been applied, such as by smearing, to the surface of an expansible membrane. After being permitted to dry, the membrane is expanded uniformly causing the cells to be isolated or pulled apart as shown in FIG. 1B. The cells shown are tissue cells, but bacteria cell isolation is represented in an identical manner.

Note that in FIG. 1A, the microscopic viewing field represented by dotted line 4 cannot view one cell at a time, but in FIG. 1B the same field can view each cell separately, and in particular, the nuclei 2 of each cell.

Any surface which can be expanded uniformly will work for this method. Such surfaces of rubber film, elastomer web, natural membranes and some plastic webs are suitable.

Referring in particular to FIGS. 2 through 2C, a sequence of steps is shown which utilizes one feature of the subject invention to perform isolation of bacterial cells at spaced locations prior to transfer to a bacterial growth culture medium. Referring first to FIG. 2, there is illustrated a relatively thin, expansible membrane 10 which is formed from a material having the general characteristic that it can be expanded or stretched relatively uniformly to increase its surface area by a factor of from 2 to 10 times. Many types of sheet rubber and plastic have this characteristic; however, in the embodiment under consideration, the membrane 10 comprises sheet rubber which is known commercially as Dental Dam Grade Light. Typically, this rubber has a light gray color and is translucent but, when expanded or stretched, it is substantially clear and transparent to light.

As used to carry out the subject method, the unstretched or unexpanded membrane 10 is inoculated on its upper surface with a small quantity of the sample material to be tested. For example, the sample can be taken from the patient by an absorbent swab and thereafter touched lightly to the surface of the membrane 10.

After the sample has been placed on the membrane and allowed to dry, the membrane is stretched or expanded in at least one direction, preferably by a factor 2 or more. The bacteria tend to adhere to the surface of the membrane and, when the membrane is expanded as shown in FIG. 2B, the bacteria are separated so that they are isolated into small separate spots on the membrane. This happens because, as the membrane expands, each point of the membrane separates uniformly from every other point thereon. As can be appreciated, this results in a uniform isolation of all of the bacteria without the necessity of careful swabbing or streaking which produces only separation at the end of the streak.

After the membrane 10 has been expanded as shown in FIG. 2B, it is maintained in the expanded condition and brought into engagement with a bacteria culture medium. As shown in FIG. 2C, a Petri dish 14 holding a desired bacterial growth medium 15 is moved lightly into engagement with the innoculated surface of membrane 10. The bacteria on membrane 10 are thus transferred to the growth medium. After the transfer of the bacteria to the growth culture media 15, the Petri dish is placed in a suitable environment for incubation of the bacteria. FIG. 2C shows the bacteria 16 growing in isolated colonies on the surface of the growth media.

The mechanism involved in producing the separation of the bacteria during the expansion of membrane 10 is believed to be a combination of the physical separation of adjacent bacteria due to the elongation or stretching of the membrane, together with a dislodging of adjacent bacteria due to stress produced during the stretching operation.

Obviously, the membrane could be mounted in many specific arrangements for facilitating the stretching of the membrane to allow further handling and the like. FIGS. 3A and 3B illustrate a frame and stretching arrangement which is particularly suited for use in microscopic examination of the isolated bacteria or other samples. As shown, the FIG. 3A apparatus includes a microscopic slide member 18 which is of elongated rectangular shape and preferably formed from transparent glass, plastic, or the like. A small section of any suitable membrane material, such as the previously mentioned Dental Dam sheeting, is attached to one end portion of the slide 18. In the embodiment shown, the sheeting 20 is connected to the end of the slide by a short section of tape 22. With this type of arrangement, it is preferable that the sample be applied by a streaking action in a direction generally transversely of the plate. Note that in FIG. 2, a sample is shown as streaked across the membrane 20 in the direction of the arrow. Thereafter, the membrane can be stretched along the slide as shown in FIG. 2A and a second section of tape 24 used to affix it in the stretched condition to the slide. The stretching action, in combination with the transverse streaking, causes the sample to be separated as shown in FIGS. 3B. With this arrangement, the sample can be viewed microscopically or, alternately, transferred to a culture medium such as described with reference to the FIGS. 2A through 2C.

The particular form of the membrane member is not of importance to the method aspects of the invention. Additionally, the manner in which the membrane is stretched is not of particular importance and any form of mechanical or fluid stretching could be utilized. For example, FIGS. 6 through 6C show how a modified form of membrane holder and stretching can be utilized. The FIG. 6 illustration shows a membrane and frame which comprises a generally circular rigid plastic frame 28 which has the generally unexpanded membrane stretched thereover and connected at its periphery to frame 28. The membrane 30 can be of any desired or suitable type of rubber or elastomeric material which is capable of undergoing the required amount of stretching. The membrane 30 is innoculated with the tissue cell or bacteria sample 32 and thereafter positioned over a mechanical plunger 34 which is mounted for vertical reciprocation either manually or automatically. Preferably, the frame 28 is mechanically held in a position over the plunger so that when the plunger is actuated upwardly, the membrane 30 will be uniformly stretched to the dotted line position shown. Any type of clips or holders 35 can be used to hold the frame 28.

After the membrane 30 has been innoculated and the sample permitted to dry, the plunger 34 is actuated upwardly moving the innoculated surface to the dotted line position and stretching it a substantial amount to cause the biological cells in the sample to become separated as shown in FIG. 6A and 1B. At this time, the isolated cells can be observed and/or automatically scanned microscopically or, alternately, transferred to a suitable growth medium. In FIG. 6B, a Petri dish 36 is shown being moved into engagement with the innoculated surface of the membrane 30. Thereafter, the Petri dish is incubated to cause the individual bacteria colony growth as shown in FIG. 6.

Figure 7:
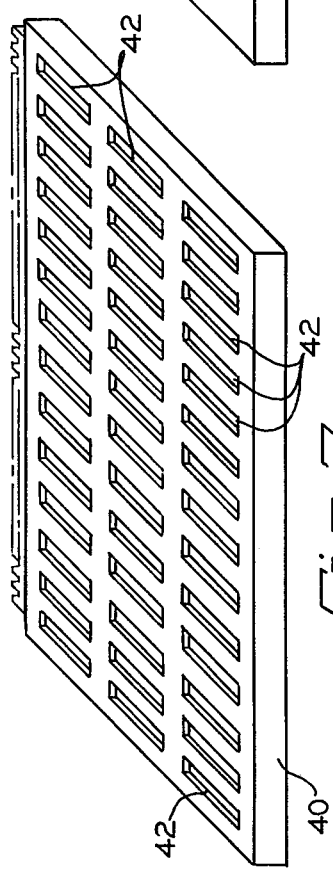
FIG. 7 is a pictorial representation of a bacterial growth culture device used in a preferred form of apparatus according to the invention.

The expanding membrane method of bacteria isolation allows automatic scanning and readout of the bacteria cultures to be carried out relatively easily. FIGS. 7 and 8 show growth media arrangements which are particularly suited for automatic scanning and readout. The FIG. 7 embodiment comprises a relatively rigid plate or thin sheet of plastic or the like 40 which has formed or molded in one surface thereof, a multiplicity of closely spaced recesses or grooves 42. The grooves 42 are preferably small and of a size such as to be able to hold growth media therein through capillary action.

It has been found that grooves of from one-sixty-fourth to one-eighth inch wide and approximately the same size in depth, and between one-fourth and one-half inch long are particularly suitable. The growth medium, which can be either a liquid or a gel, is infused into the grooves where it is normally held by capillary attraction. Additionally, a thin sheet of plastic film can be removably positioned over the open upper surface of the grooves to maintain the media in the grooves and prevent evaporation thereof. With the plastic sheet in position, the entire assemblage can be sterilized.

One advantage of this particular type of growth medium arrangement is that the grooves can have a plurality of selective growth medias positioned therein. For example, medias in certain grooves can be of a type in which particular bacteria will not grow whereas others will grow and produce a distinct color change. By proper selection of the growth medias, it is possible to permit one such growth media plate to give a substantial amount of information about the bacteria in a sample.

For example, such selective growth medias are well known and are of these general types:
1. a ph indicator and a substrate specific for a certain bacteria strain; when fermentation of the substiate begins, a ph color change occurs;
2. a blood agar which changes from red to clear when pathogenic strains are present;
3. a growth medium with a chemical color indicator specific for the metabolism products of certain bacteria strains; and,
4. fluorescent antibody preparations specific for certain bacteria strains.

When using the plate or growth medium member of FIG. 7, the cover film is removed and the plate placed in engagement with the innoculated, expanded membrane. The individual bacteria on the expanded membrane are transferred to the different growth medias with a limited number of bacteria transferred into each growth media section. Thereafter, following incubation, the manual or automatic scanning of the plate gives a readout of the type of bacteria present in the sample by noting which of the various sections produced which type of color changes and/or growth.

FIG. 8 shows a modified arrangement which uses the same general concept as discussed with reference to FIG. 7. In the FIG. 8 embodiment, the assembly includes a rectangular plastic plate 46 on which is attached a multiplicity of small individual or separated sections of absorbent material such as filter paper or the like. Each of the paper or absorbent strips 48 can be soaked with a selected growth media and the medias prevented from drying out until use by the use of a hydrophobic plastic cover film stretched over the surface.

Clearly, many types of growth media holders and arrangements could be used in combination with the expansible membrane. Additionally, other types of bacteria isolating techniques could be used with the growth media assemblies such as in FIGS. 7 and 8.

Figure 9:
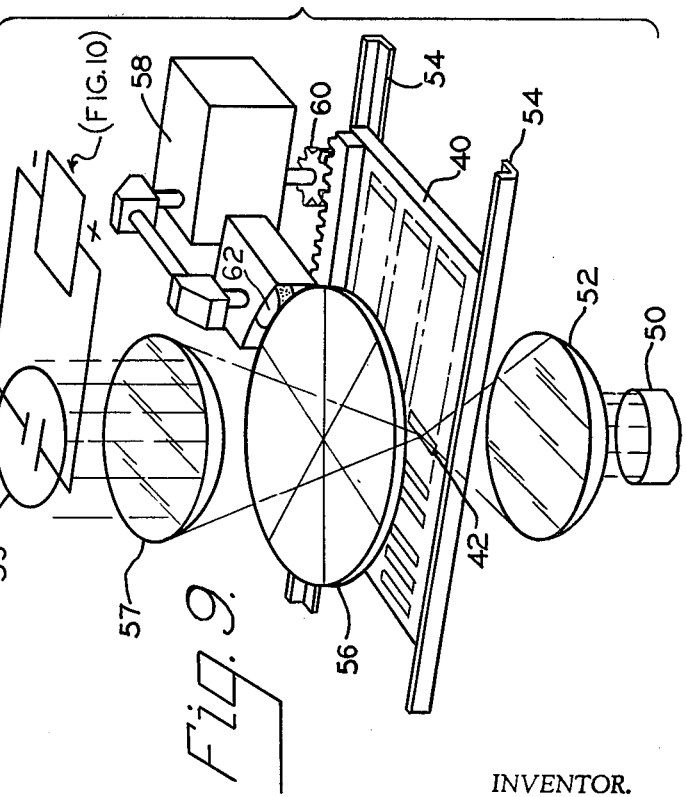
FIG. 9 is a pictorial, diagramatic representation of an apparatus for performing automatic scanning and readout of a bacterial growth apparatus of the type shown in FIG. 7.

FIG. 9 diagramically illustrates an arrangement whereby the assembly of FIG. 4 can be automatically scanned to give readout of the presence or absence of any change in each of the individual capillary grooves. In the FIG. 7 embodiment, the plate 40 of the assembly of FIG. 4 would be a clear plastic sheet through which light can freely pass. Broadly, the concept of the FIG. 9 apparatus contemplates passing a focused light beam through each of the grooves individually and passing the light which comes through the grooves through a filter. The filter is of a color such that if the growth media in the noted groove had undertaken a desired or expected color change, then the light would be filtered out and would not pass through the filter or, alternately, a distinct color would be present. Positioned opposite the filter is a light sensitive device which produces a signal if a light response was reached to indicate that a color change had not taken place. By moving the plate relative to the light source and filter, each of the grooves can be scanned and an indication given by the photo-sensitive member as to whether or not the change had taken place. By properly correlating the movement of the filter with the movement of the plate, a readout can be given for each groove in the entire plate.

Apparatus capable of performing this function is diagramatically shown in FIG. 9. Note that a light source 50 is mounted at a first location and focused by a lens member 52 mounted thereabove. growth medium plate 40 is guided above the lens 50 in any suitable means such as used through the use of guide tracks 54. As the member 40 is passed above the lens 52, the light is focused on the grooves 42. Immediately above the groove is a rotatably mounted filter disc 56. This disc is driven in a predetermined relationship relative to the plate movement by a mechanical drive assembly 58. For example, if the particular growth media in the groove under consideration elicits a red response upon action by particular bacteria strain, then a green filter would be in position above the groove. The presence or absence of light passing through the filter would indicate whether or not the color change had taken place. The assembly shown in FIG. 9 provides a second lens 57 aligned with the lens 52 and adapted to focus any light which passes through the filter against a photocell 59. The output from the photocell gives an indication of the presence or absence of light.

The particular inter-connection between the plate 40 and the filter 56 is not of importance and, for example, could be a simple mechanical gear drive comprising a rack gear section formed along one edge of the plate 40 and engaged by a pinion gear 60 connected through suitable gearing with a disc drive gear 62. As the plate 40 is moved past the gear 60, the color wheel 56 is automatically moved to the proper color filter.

Figure 10:
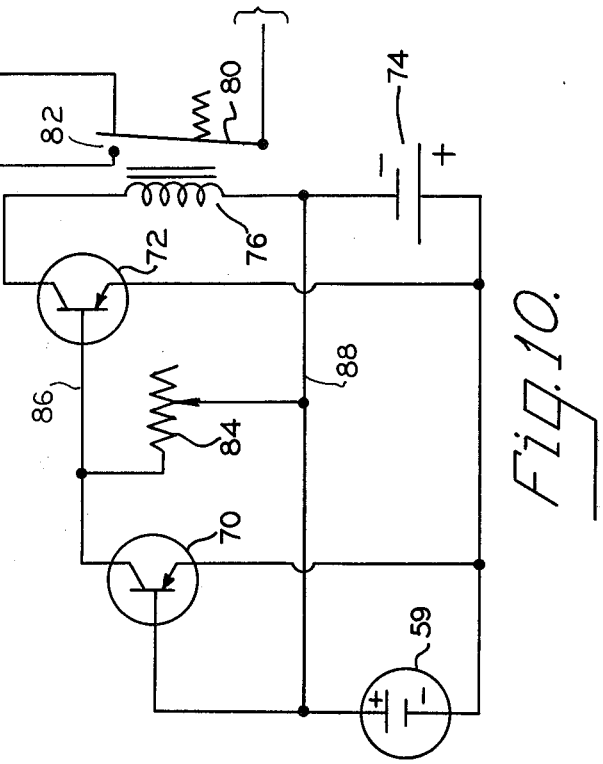
FIG. 10 is a schematic wiring diagram of the apparatus illustrated in FIG. 9.

FIG. 10 illustrates a simplified electronic circuit which could be used for providing the required output from the photocell 59. The circuit shown in FIG. 10 is a simplified arrangement for obtaining an output indicative of the presence or the absence of color change in the groove under consideration. As will be noted, the circuit includes two PNP transistor 70 and 72 which are connected to the photocell 59 in the manner shown. A battery or similar DC power source 74 is connected through a switch operating relay 76. In operation, energization of the photocell 59 causes current flow through the transistor 72 and energization of the relay 76 to move the switch arm 80 into contact with contact 82. A variable resistance 84 is connected across lines 86 and 88 to vary the output required to actuate relay 76.

Figure 11:
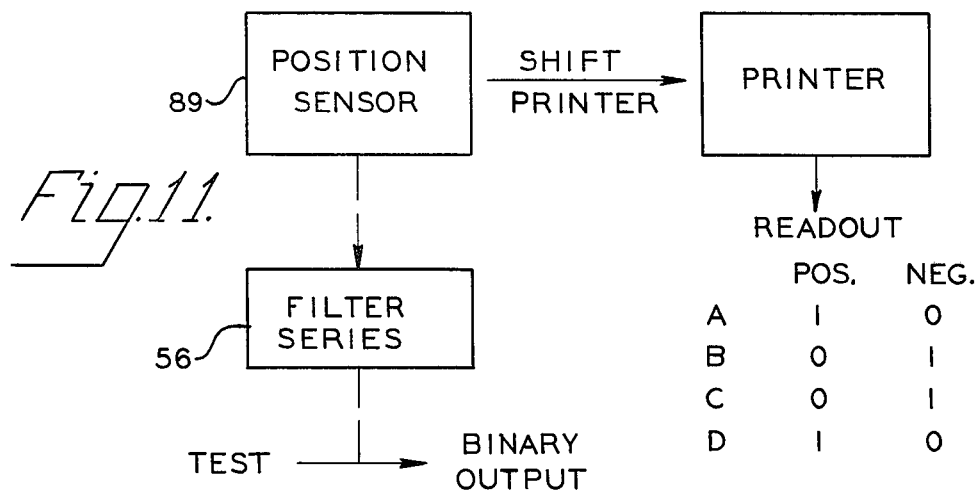
FIG. 11 is a flow diagram illustrating the sequence of operations carried out by the apparatus of FIG. 9.

Many other types of circuits could equally well be used. Additionally, any type of indicating or readout device could be associated with the switch 80. For example, the output from the switch 80 is a digital output and could be used in a system as shown schematically in FIG. 11. That is, a position sensor 89 could be provided to sense the position of the member 40 and filter wheel 56. The output from the switch 80 would then be utilized in combination with a digital printer actuated to provide a separate printout for each position of the filter and member 40.

The expansible membrane technique can also be used for performing diagnostic cytology. For example, it is known that animal tissue cells which are neoplastic have a much lower cell-to-cell adhesion. Additionally, not only do the cancerous or neoplastic cells have a lower cell-to-cell adhesion characteristic but, also, they tend to have a much higher accumulation of nucleic acids. The subject invention utilizes one or both of these characteristics to permit rapid scanning of a cell sample to determine whether or not the cells are from normal or cancerous tissue.

FIGS. 4A–4C schematically illustrate a system for use in performing tests on animal tissue cells. As shown in FIG. 4A, an exfoliate or biopsy cell sample or the like 320 (obtained with a cotton tipped stick, for example) is first smeared on membrane 310 as shown, and allowed to dry. This sample is then washed with any chemical stain 330 as shown in FIG. 4B. The membrane is then expanded isolating the cells 360 as shown in 4C. These isolated cells can then be optically scanned by scanner 340 and a voltage readout given, 350.

In addition to the visual check which is possible as shown in FIGS. 4A–4C, the membrane technique also permits the cells to be stained while they are either in the expanded or unexpanded condition. By selecting a stain which will produce a fluorescent nuclei in the cell, the large nuclei of abnormal cells provide greater fluorescence and in this way are indicative of neoplastic tissue. One type of stain solution which is used and which will produce the desired change is Acridine Orange Stain Solution which is flurochrome for nucleic acids. Assuming that an Acridine orange stain solution of the type described is to be used, the cells are flooded for a period of approximately 20 seconds with the solution and then rinsed with a calcium chloride solution for another 20 seconds. The cells are maintained wet with a PH 3.8 buffer while they are optically scanned. The stained cells can be scanned manually such as, for example, by viewing them under 600 or greater power magnification. The presence of the isolated cells together with the larger fluorescent nuclei is a rapid indication of the presence of cancerous tissue.

Figure 12:
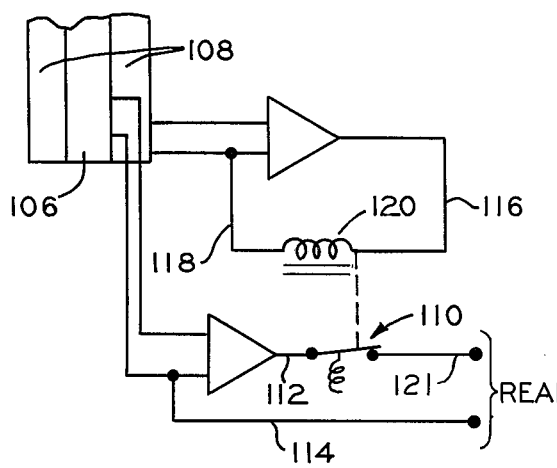
FIG. 12 is a schematic illustration of an automatic scanning apparatus which can be used for automatic scanning of tissue cells.
Figure 14:
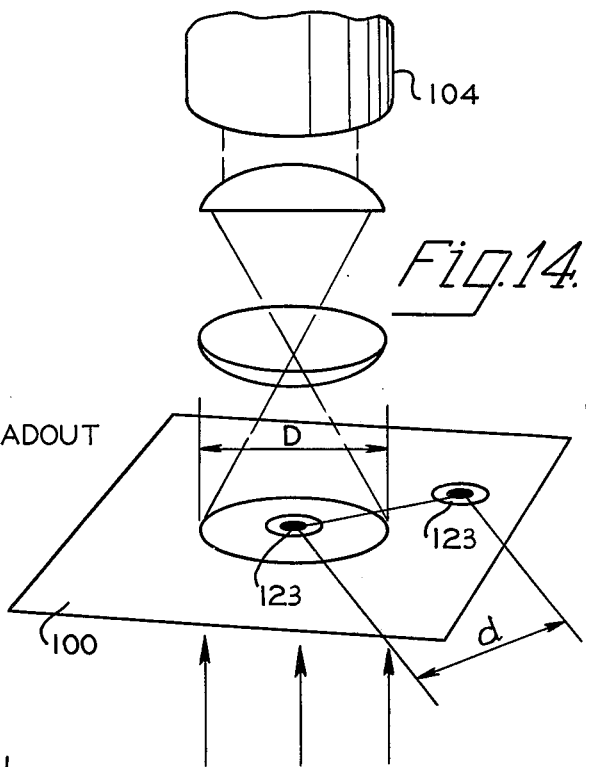
Figure 13:
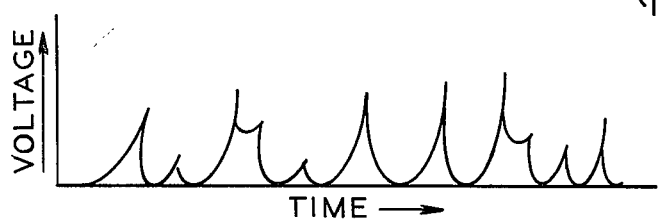
FIG. 13 is an illustration of a typical voltage wave form produced by the FIG. 12 apparatus; and, FIG. 14 is a diagramatic illustration which explains the operation of the FIG. 13 apparatus.

In addition to manual scanning, it is possible to scan the member automatically and give an output signal which is indicative of the number of free cells and/or the individual nuclei size. FIG. 12 shows a circuit which is capable of performing automatic scanning. To understand the scanning procedure carried out reference is made to FIG. 14 wherein a membrane 100 is shown with two cells 123 carried thereon. Assume that after the membrane expansion the cells are separated from each other a distance small $d$. Then, if the field focused upon by the scanner 104 has a diameter D equal to small d and the scanner moves with a forward speed of one-half large D, each scan, as it scans over the many cells on the membrane, should, at some time, pass over each cell individually. At this instant, only one cell will be in the field. If the scanner is hooked to a circuit of the type shown in FIG. 13, then it will give an output which indicates only those times when it is seeing only one whole cell in the field. As described, each cell displays a characteristic nuclear fluoescense, which is expressed in voltage level at the output of the scanner. All normal body cells have the same general level of nuclear fluorescense reference. Abnormal cells will have a higher fluorescence level and therefore an output of greater voltage. The output results are shown, for example, in FIG. 13 which is merely typical of the type of voltage levels which can be expected from this type of circuit. Note that each individual peak will represent a separate cell under the scanning field whereas the heighth of the peak will represent the level of fluorescence.

As mentioned, FIG. 12 shows a preferred form of the circuitry for providing the desired output. Note that the scanner 104 includes concentrically positioned inner and outer photocells 106 and 108. The inner photocell is connected through a first amplifier circuit with a switch 110. Whenever the inner photocell 106 is actuated, a voltage output will be present between lines 112 and 114. The outer photocell 108 is connected through the same type of amplifier circuit such that whenever a cell is sensed by photocell 108, a voltage output will be present between lines 116 and 118. Voltage across lines 116 and 118 will, however, energize a relay 120 to cause opening of switch 110 preventing the output between the lines 114 and 112 from being present at lines 121 and 114. Accordingly, only at those times when a cell is being sensed by 108 and no cell is being sensed by photocell 106, or when a single cell is sensed by 108 and not overlapping onto 106, is it possible for an output to be present at lines 121 and 114. Additionally, as can be appreciated, the level of fluorescence sensed by photocell 108 will cause a variation in voltage level.

A specific example is the screening for cervical cancer. The physician or patient herself strokes the cervical area with a cotton tipped stick according to standard medical procedure. Possible loose cancerous cells are carried off onto the stick. This sample is then simply swabbed onto the surface of the membrane. The cells on the membrane are then washed with a stain solution and isolated by membrane expansion. The cells on the membrane are then scanned with the circuit just described and a readout is given. This readout is a direct statistical diagnostic evaluation of the number of abnormal cells in the sample.

Another specific example is the diagnosis of lung cancer which differs only from the case just described by the anatomical region the sample is obtained from. Lung sputum induced by inhalation of water droplets is swabbed on the membrane.

Note that abnormal cells can easily be re-found manually by noting at what point in the scan they are detected. To facilitate this, a reference matrix can be printed on the membrane.

The invention has been described in great detail sufficient to enable one of ordinary skill in the microbiological testing art to make and use the same. Obviously, modifications and alterations of the preferred embodiment will occur upon a reading and understanding of the specification and it is my intention to include all such modifications and alterations as part of my invention insofar as they come within the scope of the appended claims.

What is claimed is:

1. A method of isolating bacterial colonies in a sample comprising the steps of:

a. providing a member having a two dimensional surface which can be expanded in at least one dimension;
b. placing a portion of said sample on said surface; and,
c. expanding said surface in said at least one dimension an amount sufficient to cause individual bacterial colonies in said sample to be separated from one another.

2. The method as defined in claim 1 including the step of providing a bacteria growth culture medium and bringing said medium into engagement with said surface after said surface has been expanded to cause the bacteria to be transferred to said medium.

3. The method as defined in claim 1 including the step of providing a member having a plurality of discrete, closely spaced, selective growth medias, carried thereon, and bringing said expanded surface into engagement with said medias.

4. The method as defined in claim 1 wherein said sample is swabbed on said surface in a first direction and said surface is expanded in a direction having a major component perpendicular to said first direction.

5. The method as defined in claim 1 wherein said sample is a liquid which is permitted to dry on said surface prior to expansion of said surface.

6. The method as defined in claim 1 including the step of expanding said surface in both dimensions.

* * * * *